(12) United States Patent
Unlu et al.

(10) Patent No.: US 10,151,680 B2
(45) Date of Patent: Dec. 11, 2018

(54) NANOPARTICLES FOR SELF REFERENCING CALIBRATION

(71) Applicant: TRUSTEES OF BOSTON UNIVERSITY, Boston, MA (US)

(72) Inventors: Selim M. Unlu, Jamaica Plain, MA (US); George Daaboul, Amesburg, MA (US); Margo R. Monroe, Cambridge, MA (US); Carlos Lopez, Brighton, MA (US); Ahmet Tuysuzoglu, Brighton, MA (US); Sunmin Ahn, La Jolla, CA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 155 days.

(21) Appl. No.: 15/032,960

(22) PCT Filed: Oct. 28, 2014

(86) PCT No.: PCT/US2014/062605
§ 371 (c)(1),
(2) Date: Apr. 28, 2016

(87) PCT Pub. No.: WO2015/065995
PCT Pub. Date: May 7, 2015

(65) Prior Publication Data
US 2016/0282253 A1    Sep. 29, 2016

Related U.S. Application Data

(60) Provisional application No. 61/896,242, filed on Oct. 28, 2013.

(51) Int. Cl.
*G01N 15/10* (2006.01)
*G02B 21/24* (2006.01)
(Continued)

(52) U.S. Cl.
CPC ....... *G01N 15/1012* (2013.01); *C12Q 1/6837* (2013.01); *G01N 15/1434* (2013.01);
(Continued)

(58) Field of Classification Search
CPC .............................. C12Q 1/6837; G01B 11/02
See application file for complete search history.

(56) References Cited

U.S. PATENT DOCUMENTS

2009/0190129 A1* 7/2009 Yguerabide ........... G01N 21/47
356/338
2013/0231260 A1* 9/2013 Lau .................. G01N 33/54353
506/9

FOREIGN PATENT DOCUMENTS

WO      2011/014282 A2    2/2011
WO    WO 2011014282 A2 *  2/2011 ......... G01B 11/0625

OTHER PUBLICATIONS

Daaboul et al., "High-throughput detection and sizing of individual low-index nanoparticles and viruses for pathogen dentification," Nano. Lett. 10(11):4727-31 (2010).
(Continued)

*Primary Examiner* — Thai Q Tran
*Assistant Examiner* — Girumsew Wendmagegn
(74) *Attorney, Agent, or Firm* — Ronald I. Eisenstein; David F. Crosby; Nixon Peabody LLP

(57) ABSTRACT

Systems and methods for high-throughput processing of assay plates include a calibration nanoparticle to facilitate automated focusing of the imaging system. An assay plate includes a base layer, a transparent layer in contact with the base layer, and at least one calibration nanoparticle having a pre-defined size immobilized on the assay plate surface. The assay plate surface can be functionalized to selectively
(Continued)

bind to biological targets. The assay plate can be used in an imaging system for high-throughput autofocus and biological target detection.

27 Claims, 10 Drawing Sheets

(51) Int. Cl.
    *C12Q 1/6837*     (2018.01)
    *G01N 15/14*     (2006.01)
    *G01N 33/543*     (2006.01)
    *G02B 7/09*     (2006.01)
    *G02B 21/02*     (2006.01)
    *G02B 21/06*     (2006.01)
    *G02B 21/34*     (2006.01)
    *G02B 21/36*     (2006.01)
    *B82Y 15/00*     (2011.01)

(52) U.S. Cl.
    CPC ......... *G01N 33/54366* (2013.01); *G02B 7/09* (2013.01); *G02B 21/02* (2013.01); *G02B 21/06* (2013.01); *G02B 21/244* (2013.01); *G02B 21/34* (2013.01); *G02B 21/365* (2013.01); *B82Y 15/00* (2013.01); *G01N 2015/1018* (2013.01); *G01N 2015/1087* (2013.01); *G01N 2015/1454* (2013.01); *Y10S 977/954* (2013.01)

(56) References Cited

OTHER PUBLICATIONS

Hennequin et al., "Optical detection and sizing of single nanoparticles using continuous wetting films," ACS Nano. 7(9):7601-9 (2013).
Mitra et al., "Real-time optical detection of single human and bacterial viruses based on dark-field interferometry," Biosens. Bioelectron. 31(1):499-504 (2012).
Monroe et al., "Single nanoparticle detection for multiplexed protein diagnostics with attomolar sensitivity in serum and unprocessed whole blood," Anal. Chem. 85(7):3698-706 (2013).
Reddington et al., "An interferometric reflectance imaging sensor for point of care viral diagnostics," IEEE Trans. Biomed. Eng., 60(12):3276-83 (2013).

* cited by examiner

FIG. 7

NANOPARTICLES FOR SELF REFERENCING CALIBRATION

CROSS-REFERENCE TO RELATED APPLICATIONS

This application is a 35 U.S.C. § 371 National Phase Entry Application of International Application No. PCT/US2014/062605 filed Oct. 28, 2014, which designates the U.S., and which claims benefit under 35 U.S.C. § 119(e) of U.S. Provisional Application No. 61/896,242 filed Oct. 28, 2013, the contents of each of which are incorporated herein by reference in their entirety.

STATEMENT REGARDING FEDERALLY SPONSORED RESEARCH

This invention was made with Government Support under Contract Nos. EB015408 and AI096159 awarded by the National Institutes of Health and Contract No. 1127833 awarded by the National Science Foundation. The Government has certain rights in the invention.

REFERENCE TO MICROFICHE APPENDIX

Not Applicable

BACKGROUND

Technical Field of the Invention

The ability to detect biological targets including bio-nanoparticles (e.g., virus and bacteria) and biomolecules (e.g., DNA, RNA, and proteins) is critical for diagnostics, bio-threat containment, and fundamental research. It is highly desirable to be able to detect low concentration of biological targets in a sample in a low-cost, reliable, quantitative, and high-throughput manner.

Optical microscopy is commonly used for bench-top detection of biological targets. Due to their small sizes, biomolecules can be selectively tagged to nanoparticles to facilitate detection. However, the detection accuracy and speed for biological targets is compromised by the difficulties of precisely focusing the microscope on the biological targets, especially in the instances when the biological targets are small. The difficulties stem from three main factors. First, during measurements, the microscope focus drifts due to ground vibration and other destabilizing factors. Ground vibration is hard to minimize or circumvent, particularly in practical settings (e.g., hospitals and clinics). Second, measurements that rely on manual focusing by the user are slow and inherently have user-induced errors. Lastly, when the concentration of the biological targets is low, the biological targets might or might not be in the field of view of the microscope. As a result, the microscope spends significant amount of time searching and locating the biological targets, hence slowing down the measurements.

SUMMARY

The present invention encompasses, inter alia, the recognition that by providing calibration nanoparticles on an assay plate surface, a microscope equipped with a computing system can perform high-speed and high-resolution autofocusing. The calibration nanoparticles can serve as a reference for the microscope to locate the optimal focal plane for biological target detection. In addition, the inventors have discovered that calibration nanoparticles can facilitate measurements in instances when few or none biological targets are present in the samples.

One aspect of the invention relates to an assay plate comprising a base layer, a transparent layer and at least one calibration nanoparticle having a pre-defined size. The base layer has a first reflective surface. The transparent layer has a first surface in contact with the first reflective surface, and a second surface providing a second reflective surface. The first and second reflective surfaces create an optical path length difference for light illuminating the assay plate. The calibration nanoparticle is immobilized in close proximity to the second surface of the transparent layer, whereby upon illumination, the sizes of the calibration nanoparticles can be determined as a function of the reflected light signal, and whereby the calibration nanoparticles can be used as markers for autofocusing.

In accordance with some embodiments of the invention, the first reflective surface can be partially reflective, wherein the transparent layer can be partially transparent and can be less than 1000 nm thick, and wherein the calibration nanoparticles can be placed in one or more calibration regions each having at least one calibration nanoparticle.

In accordance with some embodiments of the invention, the reflectivity characteristics for the two reflective surfaces and the transparency characteristics for the transparent layer are selected to provide a measurable interferometric signal.

In accordance with some embodiments of the invention, the base layer comprises silicon.

In accordance with some embodiments of the invention, the transparent layer comprises silicon oxide.

In accordance with some embodiments of the invention, the calibration nanoparticles can be immobilized on the second surface of the transparent layer through an adhesive.

In accordance with some embodiments of the invention, the adhesive includes a polymer.

In accordance with some embodiments of the invention, the calibration nanoparticles can be fabricated through lithography or focused ion beam.

In accordance with some embodiments of the invention, the calibration nanoparticles can have an average diameter in the range of 5 nm to 250 nm.

In accordance with some embodiments of the invention, the assay plate further comprises markers arranged in a periodic or predefined configuration.

In accordance with some embodiments of the invention, the assay plate further comprises probes on the same assay plate surface as the calibration nanoparticles, wherein the probes are antibodies, antigens, DNAs, RNAs, other macromolecules, and any combinations thereof.

Another aspect of the invention relates to the assay plates as described herein, the assay plates produced by a process comprising (i) immersing the layered plate in a polymer solution including calibration nanoparticles having a pre-defined size; and (ii) washing the layered plate. Optionally, the layered plate is further baked at a pre-defined temperature after step (ii).

Another aspect of the invention relates to the assay plates as described herein, the assay plates produced by a process comprising (i) immersing the layered plate in a polymer solution; (ii) washing the layered plate; and (iii) spotting with a patterning device calibration nanoparticles having a pre-defined size onto the polymer-coated layered plate. Optionally, the layered plate is further baked at a pre-defined temperature prior to step (iii).

Another aspect of the invention relates to a system comprising the assay plate as described herein and an imaging system. The system can perform autofocusing using the calibration nanoparticles on the assay plate surface. The imaging system comprises a microscope and an autofocus system. The microscope comprises an objective lens, an imaging device, and an illumination system, wherein the illumination system can separately produce at least three light sources each having a pre-defined center wavelength. The autofocus system is adapted for automatically adjusting the distance between the assay plate surface and the objective lens as a function of an image of at least one calibration nanoparticle.

In accordance with some embodiments of the invention, the illumination system comprises one or more lasers.

In accordance with some embodiments of the invention, the illumination system comprises one or more light-emitting diodes (LEDs).

In accordance with some embodiments of the invention, the illumination system comprises a white light source and at least three spectral filters.

In accordance with some embodiments of the invention, the spectral filters can each produce a beam of light having a narrow wavelength range.

In accordance with some embodiments of the invention, the narrow wavelength range is 30 nm or less.

In accordance with some embodiments of the invention, the imaging device can capture a wide-field image.

In accordance with some embodiments of the invention, the imaging device includes a CCD camera.

In accordance with some embodiments of the invention, the CCD camera is monochromatic.

In accordance with some embodiments of the invention, the CCD camera is a color camera.

In accordance with some embodiments of the invention, the autofocus system includes a motorized module that moves the objective lens with respect to the assay plate.

In accordance with some embodiments of the invention, the autofocus system includes a motorized module that moves the assay plate with respect to the objective lens.

In accordance with some embodiments of the invention, the motorized module comprises a piezo motor.

In accordance with some embodiments of the invention, the motorized module comprises a stepper motor.

A related aspect of the invention relates to a method of performing autofocusing comprising the following steps: (i) providing the assay plate as described herein; (ii) illuminating with an illumination system the surface of the assay plate using one or more light sources, and each light source is centered around one pre-defined center wavelength; (iii) imaging with an imaging device the light signal reflected from the assay plate surface and collected through an objective lens positioned at two or more different Z heights from the surface of the assay plate; (iv) determining the size of each of the calibration nanoparticles; (v) comparing the sizes of the calibration nanoparticles with a reference range, wherein the reference range is +10% to −10% of the average size of the calibration nanoparticles; (vi) determining an optimal Z height, at which the number of calibration nanoparticles falling within the reference range is maximized; and (vii) adjusting with a motorized module the assay plate surface to the optimal Z height.

In accordance with some embodiments of the invention, the method further comprises imaging with the imaging device the light signal reflected from the assay plate surface comprising unknown particles for detection.

In accordance with some embodiments of the invention, the method further comprises producing quantified information on the sizes of the unknown particles.

In accordance with some embodiments of the invention, the illumination system comprises one or more lasers.

In accordance with some embodiments of the invention, the illumination system comprises one or more light-emitting diodes (LEDs).

In accordance with some embodiments of the invention, the illumination system comprises a white light source and at least three spectral filters.

In accordance with some embodiments of the invention, the spectral filters can each produce a beam of light having a narrow wavelength range.

In accordance with some embodiments of the invention, the narrow wavelength range is 30 nm or less.

In accordance with some embodiments of the invention, the imaging device can capture a wide-field image.

In accordance with some embodiments of the invention, the imaging device includes a CCD camera.

In accordance with some embodiments of the invention, the CCD camera is monochromatic.

In accordance with some embodiments of the invention, the CCD camera is a color camera.

In accordance with some embodiments of the invention, the motorized module moves the objective lens relative to the assay plate.

In accordance with some embodiments of the invention, the motorized module moves the assay plate relative to the objective lens.

In accordance with some embodiments of the invention, the motorized module comprises a piezo motor.

In accordance with some embodiments of the invention, the motorized module comprises a stepper motor.

In accordance with some embodiments of the invention, the assay plate surface is in contact with an aqueous solution.

In accordance with some embodiments of the invention, the transparent layer of the assay plate is no more than 40 nm thick.

These and other capabilities of the invention, along with the invention itself, will be more fully understood after a review of the following figures, detailed description, and claims.

BRIEF DESCRIPTION OF THE FIGURES

The accompanying drawing figures, which are incorporated into this specification, illustrate one or more exemplary embodiments of the inventions and, together with the detailed description, serve to explain and illustrate the principles and applications of these inventions. The drawings and detailed description are illustrative, and not limiting, and can be adapted and modified without departing from the scope and spirit of the inventions.

Figure 7:
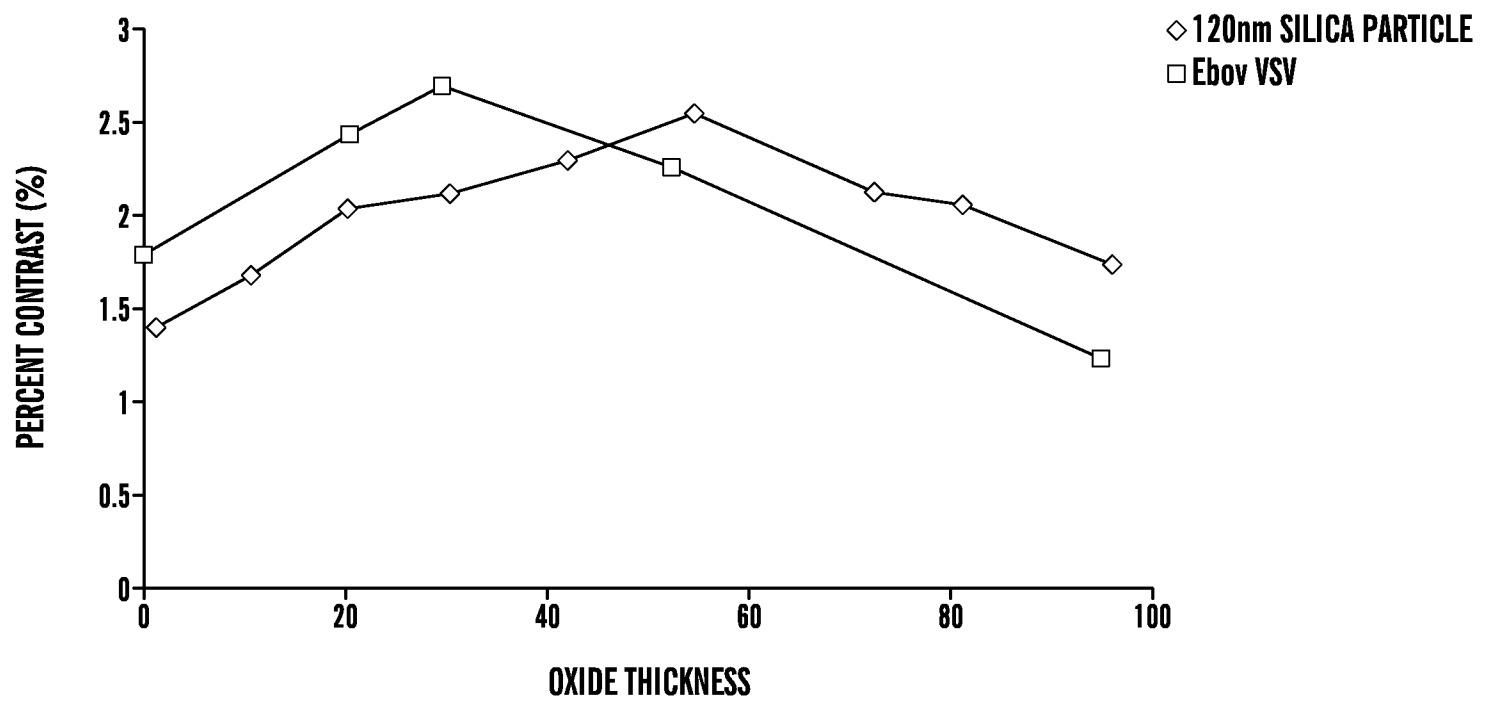

FIG. 7 is a plot of percent contrast as a function of silicon oxide thickness. The 120 nm silica particles are directly immobilized on the assay plate surface (no polymer or probes). Ebov virus particles are captured on the assay plate surface in liquid. The assay plate for Ebov virus particles is coated with polymer and antibodies, so the virus particles are positioned on top of the oxide, polymer, and antibodies.

DETAILED DESCRIPTION OF PREFERRED EMBODIMENTS

Example embodiments of various aspects are described herein in the context of an assay plate comprising calibration nanoparticles for high-speed autofocus, a system comprising an imaging system and capable of autofocus for biological target detection, and methods of use and manufacturing thereof. The inventors have discovered that by using calibration nanoparticles of known size and material properties, the calibration nanoparticles can serve as markers useful for facilitating autofocusing of the imaging system. The ability for the imaging system to perform rapid autofocusing permits high-throughput detection.

Those of ordinary skill in the art will realize that the following description of select embodiments of the invention is illustrative only and is not intended to be in any way limiting. Other embodiments will readily suggest themselves to such skilled persons having the benefit of this disclosure. Reference will now be made in detail to implementations of the example embodiments as illustrated in the accompanying drawings. The same or similar reference indicators will be used throughout the drawings and the following description to refer to the same or like items. It is understood that the phrase "an embodiment" encompasses more than one embodiment and is thus not limited to only one embodiment.

Accordingly, in some aspects, the assay plates provided herein enable a system to perform high-speed autofocusing. The system is capable of illuminating the assay plate surface with multiple wavelengths of light, recording at two or more Z heights the reflected light signals from the assay plate surface including at least one calibration nanoparticle, determining the sizes of the calibration nanoparticles at each Z height, comparing the sizes of the calibration nanoparticles with a reference size or size range, determining an optimal Z height wherein the number of calibration nanoparticles falling within the reference range is maximized, and adjusting the distance between the assay plate surface and the microscope objective lens to the optimal Z height. For biological target detection, the system can image the assay plate surface after an autofocus procedure, and produce quantitative information on the size distribution, number, and identity of the biological targets detected. As used herein, the term "Z height" refers to the height or distance between the objective lens and the assay plate in the Z direction. As used herein, the term "Z direction" or "Z axis" refers to the direction that is transverse to surface of the assay plate comprising calibration nanoparticles (as shown in FIG. 1). While in this embodiment, the assay plate is shown orientated in a horizontal configuration, in accordance with other embodiments of the invention, the assay plate can be oriented in a vertical configuration and the Z direction can be a horizontal direction.

Using a microscopy technique based on optical interferometry as described in WO2011014282, the contents of which is incorporated herein by reference in their entirety, the size of a nanoparticle made of a known material can be quantitatively correlated with the reflected light signal from the nanoparticle placed on a layered substrate. The reflected light signal from the nanoparticle in focus can be calculated based on a theoretical model. In accordance with the present invention, when the size and material properties of a nanoparticle are determined or known, the reflected light signal from the nanoparticle can indicate whether the nanoparticle is in focus.

The assay plates, methods, and systems described herein can be used in conjunction with a variety of optical microscopy techniques for the detection of biological targets. For example, once the correct focus is found using the reference particles, the optical microscopy technique as described in WO2011014282 can be performed to determine particle size and/or concentration.

It should be noted that the technology described herein is also applicable to the detection of non-biological particles such as inorganic particles, organic particles, and polymeric particles.

Assay Plate

FIG. 1A shows a cross sectional view of an assay plate 100 in accordance with some embodiments of the invention. FIG. 1B shows a top down view of the same assay plate 100. The assay plate 100 has a layered structure. The assay plate 100 can include a base layer 110, a transparent layer 120, and at least one calibration nanoparticle 130. The base layer 110 can include a first reflective surface 112 and a base surface 114. The transparent layer 120 can include a first surface 122 and a second surface 124, wherein the first surface 122 is in contact with the first reflective surface 112, and the second surface 124 can provide a second reflective surface spaced apart by a pre-defined distance from the first reflective surface 112. The calibration nanoparticles 130 can be adhered to the second reflective surface 124. In accordance with some embodiments, the calibration nanoparticle 130 can be adhered or affixed directly the second reflective surface 124. In accordance with some embodiments, the calibration nanoparticle 130 can be immobilized in close proximity with the second reflective surface 124.

The base layer 110 can be made of any material capable of partially reflecting light in the visible range. As used herein, the term "partially reflecting," "partially reflect" or "partially reflective" means at least 1%, 5%, 10%, 20%, 30%, 40%, 50%, 60%, 70%, 80%, or 90% of light in the visible range is reflected. For example, the material for the base layer 110 can include, but is not limited to, Si, GaAs GaP, GaN, InAs, InP, $GaP_xAs_{1-x}$, $InP_xAs_{1-x}$, or any combination thereof. The material can be either doped or undoped. In accordance with some embodiments of the invention, the base layer 110 can comprise Si. The first reflective surface 112 can partially reflect light in the visible range. As used herein, the term "visible range" means a spectral range of approximately 390 nm to 700 nm.

The base layer 110 can have a thickness of at least 5 nm, at least 10 nm, at least 20 nm, at least 50 nm, at least 100 nm, at least 150 nm, at least 200 nm, at least 500 nm, at least 1 μm, at least 5 μm, at least 20 μm, at least 100 μm, at least 500 μm, or at least 1000 μm.

The transparent layer 120 can comprise any material that is partially transparent in the visible range. As used herein, the term "partially transparent" means at least 1%, 5%, 10%, 20%, 30%, 40%, 50%, 60%, 70%, 80%, or 90% of light in the visible range can pass through the material. For example, the material for the transparent layer 120 can include, but is not limited to, $SiO_2$, spin-on glass, $Si_3N_4$, $Al_2O_3$, $MgF_2$, polymers (e.g., poly(methyl methacrylate), polyvinyl alcohol), or any combination thereof. The material for the transparent layer 120 can be either doped or undoped. In accordance with some embodiments of the invention, the transparent layer 120 can comprise $SiO_2$.

Figure 1A:
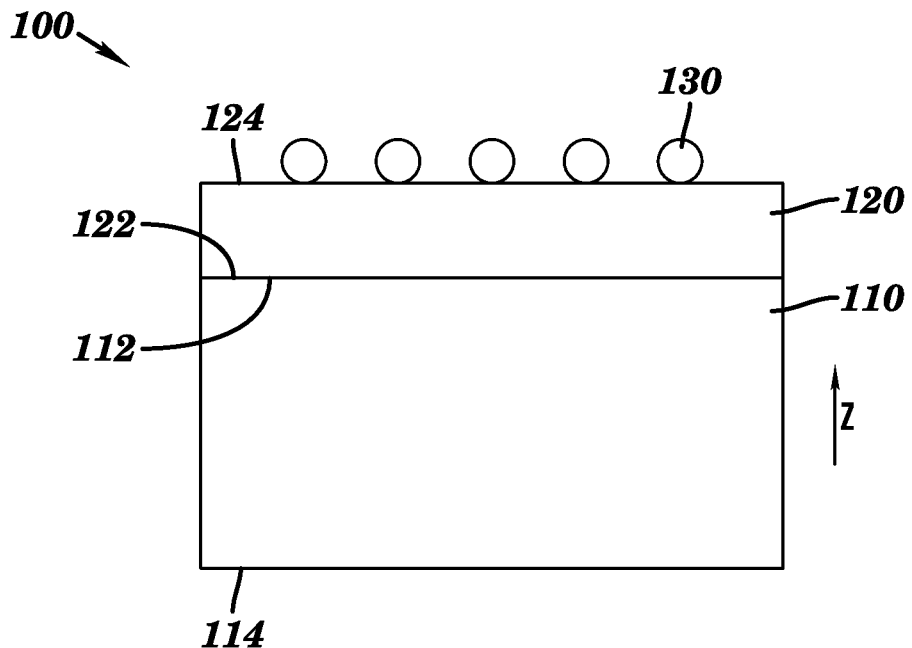
FIG. 1A shows a cross sectional view of an assay plate 100 in accordance with some embodiments of the invention.
Figure 1B:
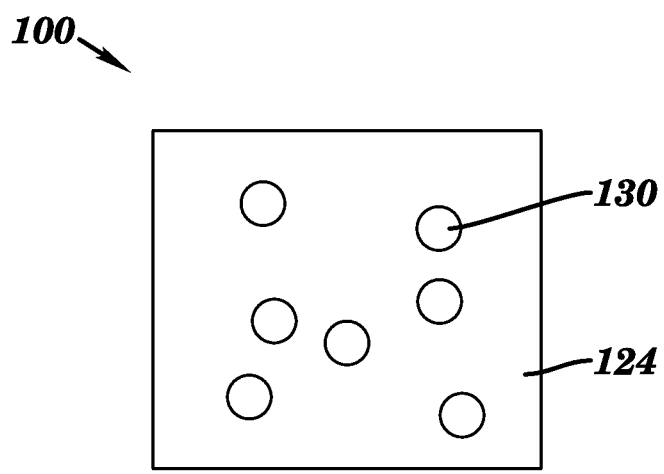
FIG. 1B shows a top down view of an assay plate 100 in accordance with some embodiments of the invention.

In accordance with some embodiments of the invention, the base layer 110 can comprise silicon and the transparent layer 120 can comprise silicon oxide.

The transparent layer 120 can have a thickness of less than 1000 nm, less than 900 nm, less than 800 nm, less than 700 nm, less than 600 nm, less than 500 nm, less than 400 nm, less than 200 nm, less than 100 nm, or less than 50 nm. In accordance with some embodiments of the invention, the transparent layer 120 can have a thickness in the range of 1 nm to 300 nm, 1 nm to 200 nm, 1 nm to 100 nm, or 1 nm to 100 nm.

The second surface 124 can be partially reflective. When light is illuminated on the assay plate surface, some portion of the light can be reflected by the second surface 124, and other portion of the light can pass through the transparent layer 120, get reflected by the first reflective surface 112 and pass through the transparent layer 120 one more time. As the light is reflected at two different surfaces (the first reflective surface 112 and the second surface 124), the optical path length difference can result in interference, an optical effect that is well-known in the art. In accordance with some embodiments of the invention, the thickness of the transparent layer 120 can be selected to maximize the interference effect in the spectral range of interest. In accordance with some embodiments of the invention, the thickness of the transparent layer 120 can be selected to maximize the signal contrast.

The reflectivity characteristics for the two reflective surfaces and the transparency characteristics for the transparent layer can be selected to provide a measurable interferometric signal. These optical characteristics can vary depending on the materials and light sources used. In accordance with some embodiments of the invention, these optical characteristics can be selected to produce an image of a calibration nanoparticle. In accordance with some embodiments of the invention, the first reflective surface can have a surface reflectivity such that it reflects light at a sufficient level to interfere with the light reflecting from the second reflective surface.

The distance between the calibration nanoparticles 130 and the second surface 124 can be determined by the process used to immobilize the calibration nanoparticles 130 to the surface. In accordance with some embodiments of the invention, the distance between the calibration nanoparticle and the second surface can be at most 100 nm, at most 75 nm, at most 50 nm, at most 40 nm, at most 30 nm, at most 20 nm, or at most 10 nm. In accordance with some embodiments of the invention, the calibration nanoparticles can be in contact with the second surface 124.

In accordance with some embodiments of the invention, the distance between the calibration nanoparticles 130 and the first reflective surface 112 can be at most 150 nm, at most 100 nm, at most 75 nm, at most 50 nm, at most 40 nm, at most 30 nm, at most 20 nm, or at most 10 nm.

The calibration nanoparticles 130 can be spatially distributed in a random or deterministic manner. In accordance with some embodiments of the invention, the calibration nanoparticles 130 can be distributed across the surface of the assay plate 100 in a periodic configuration or a random manner. The density of the calibration nanoparticles 130 can be controlled by the user depending on the specific applications. In accordance with some embodiments of the invention, the calibration nanoparticles 130 can be placed within calibrations regions. As used herein, the term "calibration region(s)" is defined as regions that have at least one calibration nanoparticle and are used for autofocusing. In accordance with some embodiments of the invention, the calibration regions do not overlap with the probe regions. As used herein, the term "probe region(s)" is defined as the areas that are functionalized with probes (e.g. antibodies, antigens, DNAs, RNAs, and other macromolecules) and are used to capture biological targets for detection. In accordance with some embodiments of the invention, the calibration regions overlap with the probe regions. The percentage of the area of a calibration region overlapping with a probe region is at least 1%, at least 5%, at least 10%, at least 20%, at least 40%, at least 60%, at least 80%, or at most 100%.

The calibration regions and probe regions can be spotted/patterned on the assay plate surface using a patterning device/method (e.g., micro-arrayer and dip pen lithography).

The shape of the calibration nanoparticles 130 can be spherical, oval, ellipsoid, rod-shaped, hexahedral, polyhedral, cuboid, or any other shapes. The calibration nanoparticle size can be in the range of 2 nm to 500 nm, 10 nm to 400 nm, 50 nm to 300 nm, or 100 nm to 200 nm. It should be noted that the calibration nanoparticle size can depend on the material properties of the calibration nanoparticles.

It will be understood by one of ordinary skill in the art that nanoparticles usually exhibit a distribution of nanoparticle sizes around the indicated "size." Unless otherwise stated, the term "nanoparticle size" as used herein refers to the mode of a size distribution of nanoparticles, i.e., the value that occurs most frequently in the size distribution. Methods for measuring the nanoparticle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In accordance with some embodiments of the invention, the calibration nanoparticles 130 can be substantially spherical. What is meant by "substantially spherical" is that the ratio of the lengths of the longest to the shortest perpendicular axes of the nanoparticle cross section is less than or equal to about 1.5. Substantially spherical does not require a line of symmetry. Further, the nanoparticles can have surface texturing, such as lines or indentations or protuberances that are small in scale when compared to the overall size of the nanoparticle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1.

For spherical particles, the diameter is at most 5 nm, at most 10 nm, at most 15 nm, at most 20 nm, at most 30 nm, at most 40 nm, at most 50 nm, at most 60 nm, at most 70 nm, at most 80 nm, at most 90 nm, at most 100 nm, at most 110 nm, at most 120 nm, at most 130 nm, at most 140 nm, at most 150 nm, at most 160 nm, at most 170 nm, at most 180 nm, at most 190 nm, at most 200 nm, at most 210 nm, at most 220 nm, at most 230 nm, at most 240 nm, at most 250 nm, at most 260 nm, at most 270 nm, at most 280 nm, at most 290 nm, at most 300 nm, or at most 500 nm.

In accordance with some embodiments of the invention, the calibration nanoparticles 130 can be made of the same material and have a narrow size distribution. In accordance with some embodiments of the invention, the sizes of at least 80% of the calibration nanoparticles can be within ±10% of a desired value. In accordance with some embodiments of the invention, the sizes of at least 85% of the calibration nanoparticles can be within ±10% of a desired value. In accordance with some embodiments of the invention, the sizes of at least 90% of the calibration nanoparticles can be within ±10% of a desired value. In accordance with some embodiments of the invention, the sizes of at least 95% of the calibration nanoparticles can be within ±10% of a desired value. In accordance with some embodiments of the invention, for a population of calibration nanoparticles having a narrow size distribution, the average size ($\bar{S}$) can be determined as follows:

$$\bar{S} = \frac{\sum_{i}^{N} S_i}{N},$$

where N is the number of calibration nanoparticles and $S_i$ (i=1 to N) is the size for nanoparticle 1 to N.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

In accordance with some embodiments of the invention, the calibration nanoparticles can be structures fabricated on the transparent layer 120 surface. The structures can be arranged in a periodic or random spatial configuration. For example, the transparent layer 120 can be etched to produce structures or features that act as calibration nanoparticles.

The calibration nanoparticles can comprise any material or combination of materials. In accordance with some embodiments of the invention, the calibration nanoparticles can be metallic (e.g., gold, silver, platinum, or copper). In accordance with some embodiments of the invention, the calibration nanoparticles can be dielectric (e.g., $SiO_2$, or $Al_2O_3$). In accordance with some embodiments of the invention, the calibration nanoparticles can be polymeric (e.g., polystyrene or polyester). Preferably, the calibration nanoparticles have similar optical properties as the particles being detected.

In accordance with some embodiments of the invention, the base surface 114 can be further in contact with a substrate layer, whereby the substrate layer can provide structural support. The substrate layer can be made of any material and can have any thickness desired by the user.

In accordance with some embodiments of the invention, the surface of the assay substrate 100 comprising the calibration nanoparticles 130 can further include periodic and micrometer-sized marks, whereby fast Fourier analysis can be performed on the periodic feature for coarse autofocusing.

In accordance with some embodiments of the invention, the surface of the assay substrate 100 comprising the calibration nanoparticles 130 can be functionalized to include probes. The probes can be designed to selectively bind to biological targets that are of interest for detection, including cells, virus, bacteria, or biomolecules that are bound to nanoparticles. Stated another way, the probes can be designed to capture biological targets from a biological sample. The probes should be in close proximity to one or more of the calibration nanoparticles so that when a biological target is captured, the biological target is not far from the calibration nanoparticles. For example, the probes can be no more than 100 µm, no more than 50 µm, no more than 25 µm, no more than 10 µm, or no more than 1 µm away from one or more of the calibration nanoparticle. Exemplary probes include, but are not limited to, an organic molecule, such as a nucleic acid, oligonucleotide, peptide, polypeptide, antigen, polyclonal antibody, monoclonal antibody, single chain antibody (scFv), F(ab) fragment, F(ab') 2 fragment, Fv fragment, small organic molecule, polymer, compounds from a combinatorial chemical library, inorganic molecule, or any combination thereof.

In accordance with some embodiments of the invention, the calibration nanoparticles can be immobilized on the second surface of the transparent layer through an adhesive such as a polymer. The calibration nanoparticles can be underneath, partially or fully embedded, or on top of the adhesive layer. In accordance with some embodiments of the invention, a first set of calibration nanoparticles is underneath the top surface of the adhesive layer and a second set of calibration nanoparticles is on top of the adhesive layer, the contrast variation of which can be used for more precise autofocusing.

In accordance with some embodiments of the invention, the calibration nanoparticles can be immobilized on the assay plate surface before the immobilization of one or more probes. In accordance with some embodiments of the invention, the assay plate can be immersed in a solution comprising the calibration nanoparticles and the probes, thereby immobilizing the calibration nanoparticles and the probes simultaneously. In accordance with some embodiments of the invention, the assay plate can be immersed in a solution comprising the calibration nanoparticles and a biological sample, thereby immobilizing the calibration nanoparticles and potential targets simultaneously.

After the assay plate is immersed in a solution comprising a biological sample, and the assay plate can be dried and cleaned, the assay plate is ready for biological target detection.

One related aspect of the invention provides a kit comprising the assay plate described herein and packaging materials.

Manufacture of the Assay Plate

Some formats of layered structures are commercially available. For example, it is well known in the art that layered structures comprising a $SiO_2$ layer in contact with a Si layer are commercially available. Layered structures can also be manufactured through methods such as ebeam evaporation, sputtering, chemical vapor deposition, physical vapor deposition, atomic layer deposition, or physical bonding.

In accordance with some embodiments of the invention, the calibration nanoparticles 130 can be immobilized to the second surface 124 using numerous surface chemistries. These chemistries can include, but are not limited to, self-assembled monolayers (e.g., silanes) or polymeric layers coated or synthesized/polymerized on the surface and are stably adhered to the surface. Generally, any type of surface chemistry can work as long as the chemistry meets the following requirements: (i) the surface chemistry is sufficiently stable under assay conditions through interactions such as covalent interactions, numerous Van Der Waals forces, hydrogen bonds, or stable binding of bio-recognition elements (e.g., biotin-streptavidin) so as to have limited or known impact on the assay; (ii) calibration nanoparticles are sufficiently stably bound through interactions such as covalent interactions, numerous Van Der Waals forces, hydrogen bonds, or stable binding of bio-recognition elements (e.g., biotin-streptavidin) so that there is limited or known impact on the autofocusing process; and (iii) surface chemistry should yield a smooth and thin (≤10 nm) layer to ensure that detection of calibration particles (or captured targets) is not compromised during particle detection and analysis.

Methods of depositing a polymer layer on a layered plate are known in the art. The specific conditions for deposition depend on the polymer type. In accordance with some embodiments of the invention, the assay plate can be produced by a process comprising: (i) immersing a layered plate in a polymer solution including calibration nanoparticles having a pre-defined size; and (ii) washing the layered plate. Optionally, the layered plate is further baked at a pre-defined temperature after step (ii).

In accordance with some embodiments of the invention, the assay plate can be produced by a process comprising: (i) immersing a layered plate in a polymer solution; (ii) washing the layered plate; and (iii) spotting with a patterning device calibration nanoparticles having a pre-defined size onto the polymer-coated layered plate. Optionally, the layered plate is further baked at a pre-defined temperature prior to step (iii).

Silane chemistries that can be applicable include, but are not limited to, epoxysilanes (e.g., glycidoxypropyl triethoxy silane), or aminosilanes (e.g., APTES), carboxyl-terminated silanes. Both monodentate and polydentate silanes can be used.

Polymers can include, but are not limited to, derivatives of acrylic-based polymers (e.g., N,N-dimethylacrylamide-methacryloyloxybenzophenone-Na-4-styrenesulfonate (Rendl et al., Langmuir 2011, 27, 6116-6123)), catecholamine derivatives (e.g., polymers conjugated to catechol-ring containing compounds such as L-3,4-dihydroxyphenylalanine (L-DOPA)). By way of examples only, an assay plate can be submerged in a polymer solution (e.g., copoly(DMA-NAS-MAPS)) mixed with calibration nanoparticles, and subsequent incubation and baking steps can result in calibration nanoparticles immobilized on the polymer-coated plate surface.

The calibration nanoparticles 130 can include chemical groups on the nanoparticle surface, wherein the chemical groups can react with the activated chemistry present on the assay plate surface. The chemical groups on the calibration nanoparticle surface can include, but are not limited to, amine, carboxyl, thiol, hydroxyl, photochemical moiety (e.g., aryl azide, benzophenone), biotin, or streptavidin, or any combinations thereof. Click chemistries can also be used to immobilize the calibration nanoparticles. For example, nanoparticles functionalized with azido groups could be used to react with alkynes present on surface.

In accordance with some embodiments of the invention, the calibration nanoparticles 130 can be fabricated on the assay plate surface through lithography (e.g., optical lithography and e-beam lithography) and material deposition, or focused ion beam.

System

Another aspect of the invention provides a system comprising the assay plate and an imaging system with autofocus capabilities, wherein the imaging system is adapted for using one or more calibration nanoparticles for automatically focusing the microscope onto the assay plate surface to detect biological targets.

Figure 2A:
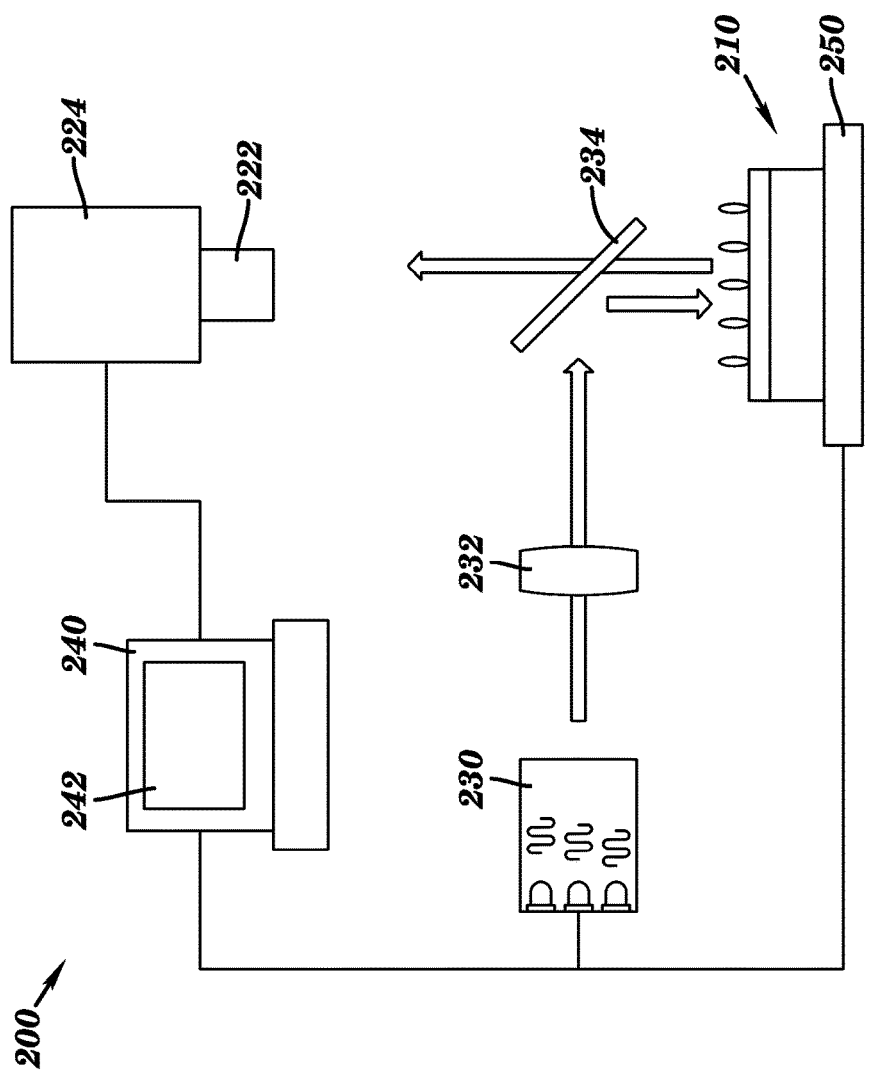
FIG. 2A shows the schematic diagram of a system 200 according to some embodiments of the invention.

FIG. 2A shows the schematic diagram of a system 200 according to some embodiments of the invention. The system 200 can include an illumination system 230 whereby the light is directed to the surface of an assay plate 210, an objective lens 222 and an imaging device 224 for capturing images of the light reflected by the assay plate 210, and a motorized module 250 supporting and enabling movement of the assay plate 210 in one, two or three dimensions. The system 200 can further include a computer system 240 for controlling the illumination system 230, receiving and processing light signals from the imaging device 224, and controlling the movement of the motorized module 250.

The illumination system 230 can provide light in at least two different center wavelengths each having a substantially narrow wavelength range. In accordance with some embodiments of the invention, the illumination system 230 can produce light in at least three different center wavelengths and as many as seven different center wavelengths. In accordance with some embodiments of the invention, the illumination system 230 provides incoherent light. In some alternative embodiments, the illumination system 230 provides coherent light.

In accordance with some embodiments of the invention, the illumination system 230 can include a plurality of illumination elements, such as Light Emitting Diodes (LEDs), lasers or equivalent light sources, each providing light in one of the plurality of center wavelengths. In accordance with some embodiments of the invention, the illumination system 230 can include an array of illumination elements, including one or more illumination elements providing light in one of the plurality of center wavelengths and being arranged in a geometric (e.g., circular or rectangular), random, or spatially displaced array with other illumination elements providing light at other center wavelengths.

In accordance with some embodiments of the invention, the illumination system 230 can include a white light source and optionally, a set of band-pass filters. A white light source is a light source with a broad optical bandwidth (usually 100 nm or more). Exemplary white light sources include, but are not limited to, red-green-blue (RGB) LEDs, phosphor-based LEDs, tungsten halogen lamps, and supercontinuum lasers. Band-pass filters are used to select light with a narrow wavelength range, the range of which is determined by the bandwidths of the filters. In accordance with some embodiments of the invention, the bandwidth is no more than 5 nm. In accordance with some embodiments of the invention, the bandwidth is no more than 10 nm. In accordance with some embodiments of the invention, the bandwidth is no more than 15 nm. In accordance with some embodiments of the invention, the bandwidth is no more than 20 nm. In accordance with some embodiments of the invention, the bandwidth is no more than 25 nm. In accordance with some embodiments of the invention, the bandwidth is no more than 30 nm. In accordance with some embodiments of the invention, the bandwidth is no more than 40 nm. The band-pass filters can be controlled by a computer system to be placed alternatively in the optical path of the white light source, thereby producing light at the desirable wavelength. It should be noted that the combination of a long-pass filter and a short-pass filter can achieve the same effect of a band-pass filter, and therefore can substitute a band-pass filter.

In accordance with some embodiments of the invention, the illumination system 230 can produce light in the visible range. In accordance with some embodiments of the invention, the illumination system 230 can produce light having center wavelengths at about 525 nm, 575 nm, and 650 nm.

The light from the illumination system 230 can be directed through a focusing lens 232 and other optical elements (e.g., polarizing lens, filters and light conditioning components, not shown) to a beam splitter 234 that directs the light onto the assay plate 210. Optical components can be provided to condition the light to uniformly illuminate substantially the entire surface of the assay plate 210. The light reflected by the assay plate 210 can be directed through the beam splitter 234 to be collected by the objective lens 222. In accordance with some embodiments of the invention, the objective 222 lens has a high magnification and a high numerical aperture.

The light is then captured and recorded by the imaging device 224. At any given moment, the imaging device 224 can image the light signal from the field of view of the device. The field of view can vary, depending on the specific device. In accordance with some embodiments, the imaging device 224 is a charge-coupled device (CCD). The CCD can be either monochromatic or color. In accordance with some embodiments of the invention, the color CCD (e.g., 3CCD) is used in conjunction with a white light source. The light signals captured and recorded by the imaging device 224 can be transmitted over a cable (or wirelessly) to the computer system 240 for further processing.

The computer system 240 can include one or more central processing units (CPUs) and associated memory (including volatile and non-volatile memory, such as, RAM, ROM, flash, optical and magnetic memory) and a display 242 for presenting information to a user. The memory can store one or more computer programs that can be executed by the CPUs to store and process the image data and produce images of the plate surface. Additional computer programs can be provided for storing, processing, and analyzing the image data.

The computer programs can be executed by the computer system 240 to implement a method according to one or more embodiments of the present invention whereby interferometric measurements can be made. The computer programs can control the illumination system 230 that can be used to illuminate the assay plate 210. The computer programs can control the illumination system 230 in order to produce light of distinct center wavelengths sequentially or all at the same time. The computer programs can control the movement of the motorized module 250 in order to adjust the distance between the surface of the assay plate 210 and the objective lens 222 for autofocusing.

In accordance with some embodiments of the invention, the computer programs can achieve autofocus by implementing a rapid focusing mechanism. See Reddington et al. IEEE Transactions on Biomedical Engineering 2013, PP (99), the contents of which are incorporated herein by reference in their entirety. Briefly, the rapid focusing mechanism can include a coarse focusing algorithm and a nanoparticle detection feedback algorithm for fine focus. During the execution of the coarse focusing algorithm, the stage carrying the assay plate can be moved over a distance (e.g., about 30 μm) along the Z axis while acquiring an image at every motion increment, e.g. a micrometer, wherein the Z axis is shown in FIG. 1A. A fast Fourier transform can be applied to the stack of the images followed by a high pass filter. The remaining high frequencies are summed. The most in-focus plane corresponds to the maximum sum. The motorized module 250 then moves the assay plate 210 to the plane that corresponds to the maximum sum. The coarse focusing algorithm can then be repeated over a smaller distance, for example, about 2 μm along the Z axis while acquiring an image every 100 nm. The same fast Fourier analysis can be applied and the surface of the assay plate 210 can be moved closer to the optimal focal plane. Subsequently, during the execution of the nanoparticle detection feedback algorithm, the assay plate 210 can be moved within ±300 nm along the Z axis of its present (coarse focus) location while acquiring an image every 100 nm or less. Each image is then processed to detect and size the calibration nanoparticles. The assay plate 210 can be moved to the optimal Z height, which is determined by maximizing the number of calibration nanoparticles within the desired particle size range.

It should be noted that the assay plate movement ranges for both coarse and fine focusing can vary as desired by the user. It should also be noted that the motion increment per image can vary from one autofocus event to the next as well as within a single autofocus event, as desired by the user. Without wishing to be bound by theory, the larger the range of motion, the longer it takes to achieve autofocusing; the smaller the motion increment, the longer it takes to achieve autofocusing. The autofocus process can be optimized by selecting the smallest range of motion and largest motion increment to achieve the desired level of autofocus.

Figure 2B:
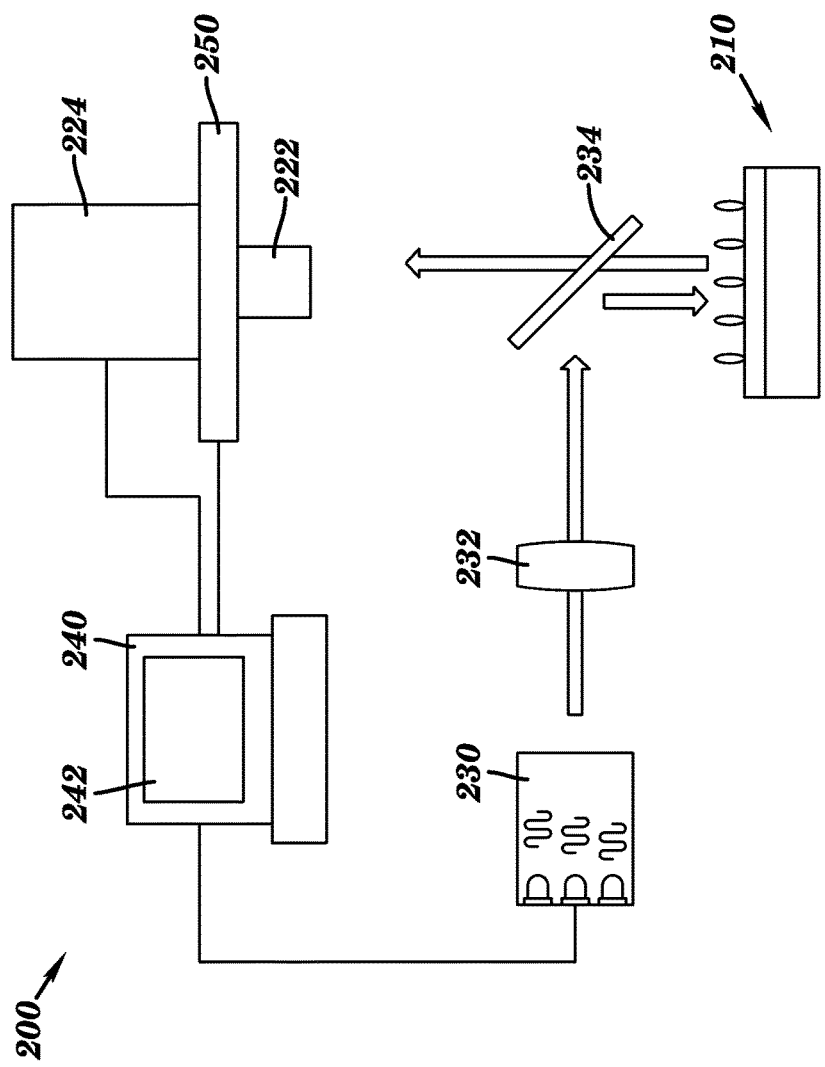
FIG. 2B shows the schematic diagram of a system 200 according to some embodiments of the invention.

In accordance with some embodiments of the invention, as shown in FIG. 2B, the motorized module 250 can be coupled to the objective lens 222, thereby allowing the motorized module 250 to control the movement of the objective lens 222 relative to the assay plate 210.

In accordance with some embodiments of the invention, the motorized module 250 can comprise a piezo motor. In accordance with some embodiments of the invention, the motorized module 250 can comprise a stepper motor. In accordance with some embodiments of the invention, the motorized module 250 can comprise a piezo motor and a stepper motor.

All embodiments of the invention can be described through functional modules, which are defined by computer executable instructions recorded on computer readable media and which cause a computer to perform method steps when executed. The modules have been segregated by function for the sake of clarity. However, it should be understood that the modules need not correspond to discrete blocks of code and the described functions can be carried out by the execution of various code portions stored on various media and executed at various times.

In accordance with some embodiments of the invention, the invention provides an autofocus system for image calibration and biological target detection, comprising a) a determination module configured to determine optical information, wherein the optical information comprises sampling different wavelengths using an illumination system covering different spectral windows; b) a storage module configured to store data output from the determination module, the data being retrievable from the storage module; c) a display module for displaying a page of the retrieved content for the user on the computer, wherein the retrieved content is in the form of a wide-field image of reflected light signals from the assay plate surface; d) a processing module configured to analyze the data stored on the storage module and produce sizing information about the calibration nanoparticles; e) a comparison module adapted to compare the quantitative results produced by the processing module with a reference range; and f) an adjustment module comprising autofocus algorithms, adapted to automatically focus the microscope onto the assay plate surface. As used herein, the reference range can be 30% to −30%, 20% to −20%, 10% to −10%, 5% to −5%, or 2% to −2% of the average size of the calibration nanoparticles.

In accordance with some embodiments of the invention, the invention provides a computer program comprising a computer readable media or memory having computer readable instructions recorded thereon to define software modules for implementing a method on a computer, said method comprising a) determining with the determination module optical information, wherein the optical information comprises sampling different wavelengths using an illumination system covering different spectral windows; b) storing with the storage module data output from the determination module, the data being retrievable from the storage module; c) displaying with the display module a page of the retrieved content for the user on the computer, wherein the retrieved content is in the form of a wide-field image of reflected light signals from the assay plate surface; d) analyzing with the processing module the data stored on the storage module and producing sizing information about the calibration nanoparticles; e) comparing with the comparison module the sizing information with a reference range; and f) adjusting with the adjustment module the distance between the assay plate surface and the objective.

The "computer readable medium" can include data and computer-executable instructions for performing the steps of the method of the invention. Suitable computer readable media include floppy disk, CD-ROM/DVD/DVD-ROM, hard-disk drive, flash memory, ROM/RAM, magnetic tapes and etc. The computer executable instructions can be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

The determination module can include computer executable instructions to determine and provide optical information using an optical instrument. As used herein, an "optical instrument" refers to any instrument that either processes light waves to enhance an image for viewing, or analyzes light waves (or photons) to determine one of a number of characteristic optical properties.

Known determination modules for determining optical properties include, for example, but are not limited to, microscopes, cameras, interferometers (for measuring the interference properties of light waves), photometers (for measuring light intensity); polarimeters (for measuring dispersion or rotation of polarized light), reflectometers (for measuring the reflectivity of a surface or object), refractometers (for measuring refractive index of various materials), spectrometers or monochromators (for generating or measuring a portion of the optical spectrum, for the purpose of chemical or material analysis), autocollimators (used to measure angular deflections), and vertometers (used to determine refractive power of lenses such as glasses, contact lenses and magnifier lens).

The optical information determined in the determination module can be stored in the storage module. As used herein, the "storage module" is intended to include any suitable computing or processing apparatus or other device configured or adapted for storing data or information. Examples of storage devices suitable for use with the present invention include stand-alone computing apparatus; communications networks, including local area networks (LAN), wide area networks (WAN), Internet, Intranet, and Extranet; and local and distributed processing systems. Storage devices also include, but are not limited to: magnetic storage media, such as floppy discs, hard disc storage medium, and magnetic tape; optical storage media such as compact disc, DVD and Blu-ray™ discs; electronic storage media such as RAM, ROM, EPROM, EEPROM, solid state storage media and the like; general hard disks and hybrids of these categories such as magnetic/optical storage media. The data are typically provided in digital form that can be transmitted and read electronically, e.g., via the Internet, on diskette, or any other mode of electronic or non-electronic communication.

As used herein, "stored" refers to a process for storing information on the storage module such that it can be read back from the module at a later time. Those skilled in the art can readily adopt any of the presently known methods for recording information on known media to generate manufactures comprising the sequence information or expression level information.

A variety of software programs and formats can be used to store the optical information on the storage device, the optical information being retrievable from the storage device. Any number of data processor structuring formats (e.g., text file or database) can be employed to obtain or create a medium having the information recorded thereon.

A page of the retrieved content can then be displayed through a display module. As used herein, the display module is intended to include suitable display apparatus, such as paper, screens, or monitors.

By providing optical information in a computer-readable form, one can further process and analyze the optical information in a readable form to produce quantitative results. As used herein, the "processing module" can include any suitable computing or processing apparatus or programs configured to perform quantitative analysis. For example, using the reflected light signals from the calibration nanoparticles, the processing module can produce quantitative results about the calibration nanoparticles. The quantitative results can also include information such as the position or size of each of the calibration nanoparticles. Some or all of the quantitative results can be displayed through the display module.

As used herein, the "comparison module" can include any suitable computing or processing apparatus or programs configured to perform the task of comparison as described herein.

The adjustment module allows a computer to control the motorized module based on an autofocus mechanism. The adjustment module can include computer executable instructions.

After autofocus is completed, the microscope is ready to detect biological targets. Under illumination by light having at least three distinct center wavelengths, the imaging system captures the light signals reflected from the assay substrate surface that may or may not contain biological targets. The processing module can then produce quantitative information on the number and sizes of the detected targets as a function of light signals reflected from the targets. A user can also deduce the identity of the targets being detected. Because focus is performed automatically, the detection of the biological targets can be done in a high-throughput manner. For example, controlled by a computing system, two or more assay plates can be run in parallel or in series with minimal human intervention.

Methods of Use

The assay plates and systems described herein can be used for autofocusing prior to the detection of biological molecules or particles in a biological sample.

In one aspect, the invention provides a method of autofocusing, the method comprising: (i) illuminating with an illumination system the surface of the assay plate using one or more light sources, wherein each light source is centered around one pre-defined center wavelength; (ii) imaging with an imaging device the light signal reflected from the assay plate surface and collected through an objective lens positioned at two or more different Z heights from the surface of the assay plate; (iii) determining the size of each of the calibration nanoparticles; (iv) comparing the sizes of the calibration nanoparticles with a reference range; (v) determining an optimal Z height, wherein the number of calibration nanoparticles falling within the reference range is maximized; and (vi) adjusting with a motorized module the assay plate surface to the optimal Z height.

In accordance with some embodiments of the invention, the reference range is +30% to −30% of the average size of the calibration nanoparticles. More preferably, in accordance with some embodiments of the invention, the reference range is +20% to −20%, +10% to −10%, +5% to −5%, +2% to −2%, of the average size of the calibration nanoparticles.

In accordance with some embodiments of the invention, autofocusing can be performed on the assay plate without biological targets, which can be subsequently introduced for detection. In accordance with alternative embodiments of the invention, autofocusing can be performed on the assay plate to which biological targets are already bound. To facilitate particle detection, the size of the calibration nanoparticles should be sufficiently different from the size distribution of particles being detected. Preferably, the calibration nanoparticles should have a size larger than the average size of particles being detected, such as 10%-100% larger, 10%-90% larger, 10%-80% larger, 10%-70% larger, 10%-60% larger, or 10%-50% larger. For example, for a virus particle having a size distribution of 100-130 nm, the calibration nanoparticles can be about 160 nm in size.

The assay plates can be used in a dry state or a wet state. When used in a wet state, the assay plate surface can be in contact with an aqueous solution. For example, an aqueous solution comprising biological targets can be introduced to the assay plate surface by drop casting or a microfluidic channel, permitting real-time measurements. When the assay plate surface is wet, the distance between the bound biological target and the assay plate surface can change compared to the dry state, for example, due to the swelling of polymer on the surface and/or probe orientation change. This challenge for particle detection can be overcome through the use of calibration nanoparticles to aid in autofocusing according to the invention.

In accordance with some embodiments of the invention, the transparent layer thickness of an assay plate used in a wet state can be less than 50 nm. In accordance with some embodiments of the invention, the transparent layer thickness of an assay plate used in a wet state can be similar to the thickness of native oxides (about 1 nm to 10 Å) on a silicon surface.

In accordance with some embodiments of the invention, the method further comprises, after step (vi), imaging with the imaging device the light signal reflected from the assay plate surface comprising unknown particles for detection. Quantified information about the unknown particles such as size, number of captured particles, and concentration of the particles can be produced.

Some embodiments of the invention are listed in the following numbered paragraphs:

paragraph 1. An assay plate comprising
(i) a base layer having a first reflective surface;
(ii) a transparent layer having a first surface in contact with the first reflective surface of the base layer, and a second surface providing a second reflective surface on the opposite side of the first surface, whereby the first and second reflective surfaces create an optical path length difference for light illuminating the assay plate; and
(iii) at least one calibration nanoparticle having a pre-defined size immobilized in close proximity to the second surface of the transparent layer, whereby upon illumination, the sizes of the calibration nanoparticles can be determined as a function of the reflected light signal, and whereby the calibration nanoparticles are used as markers for autofocusing.

paragraph 2. The assay plate of paragraph 1, wherein the first reflective surface is partially reflective, wherein the transparent layer is partially transparent and is less than 1000 nm thick, and wherein the calibration nanoparticles are placed in one or more calibration regions each having at least one calibration nanoparticle.

paragraph 3. The assay plate of paragraph 1 or 2, wherein the reflectivity characteristics for the two reflective surfaces and the transparency characteristics for the transparent layer are selected to provide a measurable interferometric signal.

paragraph 4. The assay plate of any one of the proceeding paragraphs, wherein the base layer comprises silicon.

paragraph 5. The assay plate of any one of the proceeding paragraphs, wherein the transparent layer comprises silicon oxide.

paragraph 6. The assay plate of any one of the proceeding paragraphs, wherein the calibration nanoparticles are immobilized on the second surface of the transparent layer through an adhesive.

paragraph 7. The assay plate of paragraph 6, wherein the adhesive includes a polymer.

paragraph 8. The assay plate of any one of the proceeding paragraphs, wherein the calibration nanoparticles are fabricated through lithography or focused ion beam.

paragraph 9. The assay plate of any one of the proceeding paragraphs, wherein the calibration nanoparticles have an average diameter in the range of 5 nm to 250 nm.

paragraph 10. The assay plate of any one of the proceeding paragraphs, further comprising periodic markers.

paragraph 11. The assay plate of any one of the proceeding paragraphs, further comprising probes on the same assay plate surface as the calibration nanoparticles, wherein the probes are antibodies, antigens, DNAs, RNAs, other macromolecules, and any combinations thereof.

paragraph 12. An assay plate produced by a process of immobilizing at least one calibration nanoparticle having a pre-defined size on a layered plate, wherein the layered plate comprises
(i) a base layer having a first reflective surface;
(ii) a transparent layer having a first surface in contact with the first reflective surface of the base layer, and a second surface providing a second reflective surface on the opposite side of the first surface, whereby the first and second reflective surfaces create an optical path length difference for light illuminating the assay plate. And the process comprising
(i) immersing the layered plate in a polymer solution including calibration nanoparticles having a pre-defined size; and
(ii) washing the layered plate.

paragraph 13. An assay plate produced by a process of immobilizing at least one calibration nanoparticle having a pre-defined size on a layered plate, wherein the layered plate comprises
(i) a base layer having a first reflective surface;
(ii) a transparent layer having a first surface in contact with the first reflective surface of the base layer, and a second surface providing a second reflective surface on the opposite side of the first surface, whereby the first and second reflective surfaces create an optical path length difference for light illuminating the assay plate. And the process comprising
(i) immersing the layered plate in a polymer solution;
(ii) washing the layered plate; and
(iii) spotting with a patterning device calibration nanoparticles having a pre-defined size onto the polymer-coated layered plate.

paragraph 14. A system comprising
(i) an assay plate comprising
  (a) a base layer having a first reflective surface;
  (b) a transparent layer having a first surface in contact with the first reflective surface of the base layer, and a second surface providing a second reflective surface on the opposite side of the first surface, whereby the first and second reflective surfaces create an optical path length difference for light illuminating the assay plate; and
  (c) at least one calibration nanoparticle having a pre-defined size immobilized in close proximity to the second surface of the transparent layer, whereby upon illumination, the sizes of the calibration nanoparticles can be determined as a function of the reflected light signal, and whereby the calibration nanoparticles are used as markers for autofocusing.
(ii) an imaging system comprising
  (a) a microscope comprising an objective lens, an imaging device, and an illumination system, wherein the illumination system can separately produce at least three light sources each having a pre-defined center wavelength; and
  (b) an autofocus system adapted for automatically adjusting the distance between the assay plate surface and the objective as a function of an image of at least one calibration nanoparticle.

paragraph 15. The system of paragraph 14, wherein the first reflective surface is partially reflective, wherein the transparent layer is partially transparent and is less than 1000 nm thick, and wherein the calibration nanoparticles are placed in one or more calibration regions each having at least one calibration nanoparticle.

paragraph 16. The system of paragraph 14 or 15, wherein the reflectivity characteristics for the two reflective surfaces and the transparency characteristics for the transparent layer are selected to provide a measurable interferometric signal.

paragraph 17. The system of any of paragraphs 14-16, wherein the base layer comprises silicon.

paragraph 18. The system of any of paragraphs 14-17, wherein the transparent layer comprises silicon oxide.

paragraph 19. The system of any of paragraphs 14-18, wherein the calibration nanoparticles are immobilized on the second surface of the transparent layer through an adhesive.

paragraph 20. The system of paragraph 19, wherein the adhesive includes a polymer.

paragraph 21. The system of any of paragraphs 14-20, wherein the calibration nanoparticles are fabricated through lithography or focused ion beam.

paragraph 22. The system of any of paragraphs 14-21, wherein the calibration nanoparticles have an average diameter in the range of 5 nm to 250 nm.

paragraph 23. The system of any of paragraphs 14-22, further comprising periodic markers.

paragraph 24. The system of any of paragraphs 14-23, further comprising probes on the same assay plate surface as the calibration nanoparticles, wherein the probes are antibodies, antigens, DNAs, RNAs, other macromolecules, and any combinations thereof.

paragraph 25. The system of any of paragraphs 14-24, wherein the illumination system comprises one or more lasers.

paragraph 26. The system of any of paragraphs 14-25, wherein the illumination system comprises one or more light-emitting diodes (LEDs).

paragraph 27. The system of any of paragraphs 14-26, wherein the illumination system comprises a white light source and at least three spectral filters.

paragraph 28. The system of paragraph 27, wherein the spectral filters can each produce a beam of light having a narrow wavelength range.

paragraph 29. The system of paragraph 28, wherein the narrow wavelength range is 30 nm or less.

paragraph 30. The system of any of paragraphs 14-29, wherein the imaging device can capture a wide-field image.

paragraph 31. The system of any of paragraphs 14-30, wherein the imaging device includes a CCD camera.

paragraph 32. The system of paragraph 31, wherein the CCD camera is monochromatic.

paragraph 33. The system of paragraph 31, wherein the CCD camera is a color camera.

paragraph 34. The system of any of paragraphs 14-33, wherein the autofocus system includes a motorized module that moves the objective lens with respect to the assay plate.

paragraph 35. The system of any of paragraphs 14-34, wherein the autofocus system includes a motorized module that moves the assay plate with respect to the objective lens.

paragraph 36. The system of paragraph 35, wherein the motorized module comprises a piezo motor.

paragraph 37. The system of paragraph 35, wherein the motorized module comprises a stepper motor.

paragraph 38. A method comprising
(i) providing an assay plate comprising at least one calibration nanoparticle having a pre-defined size, whereby the calibration nanoparticles are used for autofocusing;
(ii) illuminating with an illumination system the surface of the assay plate using one or more light sources, wherein each light source is centered around one pre-defined center wavelength;
(iii) imaging with an imaging device the light signal reflected from the assay plate surface and collected through an objective lens positioned at two or more different Z heights from the surface of the assay plate;

(iv) determining the size of each of the calibration nanoparticles;
(v) comparing the sizes of the calibration nanoparticles with a reference range, wherein the reference range is +10% to −10% of the average size of the calibration nanoparticles;
(vi) determining an optimal Z height, wherein the number of calibration nanoparticles falling within the reference range is maximized; and
(vii) adjusting with a motorized module the assay plate surface to the optimal Z height.

paragraph 39. The method of paragraph 38, further comprising imaging with the imaging device the light signal reflected from the assay plate surface comprising unknown particles for detection.

paragraph 40. The method of paragraph 38 or 39, further comprising producing quantified information on the sizes of the unknown particles.

paragraph 41. The method of any of paragraphs 38-40, wherein the assay plate comprises
(i) a base layer having a first reflective surface;
(ii) a transparent layer having a first surface in contact with the first reflective surface of the base layer, and a second surface providing a second reflective surface on the opposite side of the first surface, whereby the first and second reflective surfaces create an optical path length difference for light illuminating the assay plate; and
(iii) at least one calibration nanoparticle having a predefined size immobilized in close proximity to the second surface of the transparent layer, whereby upon illumination, the sizes of the calibration nanoparticles can be determined as a function of the reflected light signal, and whereby the calibration nanoparticles are used as markers for autofocusing.

paragraph 42. The method of paragraph 41, wherein the first reflective surface is partially reflective, wherein the transparent layer is partially transparent and is less than 1000 nm thick, and wherein the calibration nanoparticles are placed in one or more calibration regions each having at least one calibration nanoparticle.

paragraph 43. The method of paragraph 41 or 42, wherein the reflectivity characteristics for the two reflective surfaces and the transparency characteristics for the transparent layer are selected to provide a measurable interferometric signal.

paragraph 44. The method of any of paragraphs 41-43, wherein the base layer comprises silicon.

paragraph 45. The method of any of paragraphs 41-44, wherein the transparent layer comprises silicon oxide.

paragraph 46. The method of any of paragraphs 41-45, wherein the calibration nanoparticles are immobilized on the second surface of the transparent layer through an adhesive.

paragraph 47. The method of paragraph 46, wherein the adhesive includes a polymer.

paragraph 48. The method of any of paragraphs 41-47, wherein the calibration nanoparticles are fabricated through lithography or focused ion beam.

paragraph 49. The method of any of paragraphs 41-48, wherein the calibration nanoparticles have an average diameter in the range of 5 nm to 250 nm.

paragraph 50. The method of any of paragraphs 41-49, further comprising periodic markers.

paragraph 51. The method of any of paragraphs 41-50, further comprising probes on the same assay plate surface as the calibration nanoparticles, wherein the probes are antibodies, antigens, DNAs, RNAs, other macromolecules, and any combinations thereof.

paragraph 52. The method of any of paragraphs 38-51, wherein the illumination system comprises one or more lasers.

paragraph 53. The method of any of paragraphs 38-52, wherein the illumination system comprises one or more light-emitting diodes (LEDs).

paragraph 54. The method any of paragraphs 38-53, wherein the illumination system comprises a white light source and at least three spectral filters.

paragraph 55. The method of paragraph 54, wherein the spectral filters can each produce a beam of light having a narrow wavelength range.

paragraph 56. The method of paragraph 55, wherein the narrow wavelength range is 30 nm or less.

paragraph 57. The method of any of paragraphs 38-56, wherein the imaging device can capture a wide-field image.

paragraph 58. The method of any of paragraphs 38-57, wherein the imaging device includes a CCD camera.

paragraph 59. The method of paragraph 58, wherein the CCD camera is monochromatic.

paragraph 60. The method of paragraph 58, wherein the CCD camera is a color camera.

paragraph 61. The method of any of paragraphs 38-60, wherein the motorized module moves the objective lens relative to the assay plate.

paragraph 62. The method of any of paragraphs 38-61, wherein the motorized module moves the assay plate relative to the objective lens.

paragraph 63. The method of paragraph 62, wherein the motorized module comprises a piezo motor.

paragraph 64. The method of paragraph 62, wherein the motorized module comprises a stepper motor.

paragraph 65. The method of any of paragraphs 38-64, wherein the assay plate surface is in contact with an aqueous solution.

paragraph 66. The method of paragraph 65, wherein the transparent layer of the assay plate is no more than 40 nm thick.

Definitions

As used herein the terms "sample" or "biological sample" means any sample, including, but not limited to cells, organisms, lysed cells, cellular extracts, nuclear extracts, components of cells or organisms, extracellular fluid, media in which cells are cultured, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears and prostatic fluid. In addition, a sample can be a viral or bacterial sample, a sample obtained from an environmental source, such as a body of polluted water, an air sample, or a soil sample, as well as a food industry sample.

As used herein, the term "biological target" refers to a substance of biological origin to be detected. Non limiting examples of the biological target are proteins, peptides, antibodies, lipids, amino acids, amines, messenger or small molecules, carbohydrates, cellular components, viruses, bacteria, components of the extracellular matrix, cells, cell fragments, nucleic acids, and haptens.

The articles "a" and "an" are used herein to refer to one or more than one (i.e., at least one) of the grammatical object of the article. By way of example, "an element" means one element or more than one element. Thus, in this specification and the appended claims, the singular forms "a," "an," and "the" include plural references unless the context clearly dictates otherwise.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. As used herein the term "consisting essentially of" refers to those elements required for a given embodiment. The term permits the presence of elements that do not materially affect the basic and novel or functional characteristic(s) of that embodiment of the invention. Other than in the operating examples, or where otherwise indicated, all numbers expressing quantities of ingredients or reaction conditions used herein should be understood as modified in all instances by the term "about." The term "about" when used in connection with percentages can mean ±5%.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1: Exemplary Methods for Calibration Nanoparticles Immobilization onto the Assay Plate Surface Blanket Coating.

Gold nanoparticles are used as calibration nanoparticles. Gold nanoparticles having a narrow size distribution are commercially available (e.g., Ted Pella, Inc.). Provided herein is an exemplary protocol to immobilize the gold nanoparticles onto the assay plate surface:

Prepare a solution of copoly(DMA-NAS-MAPS) by adding 100 mg of the copolymer to 5 mL of deionized (DI) water and add 5 mL of 40% saturated ammonium sulfate (($NH_4)_2SO_4$) solution to reach a final concentration of 0.92 M. The synthesis and coating process of copoly(DMA-NAS-MAPS) can be found in Pirri et al., Anal. Chem. 2004, 76, 1352-58.

Add $NH_2$ functionalized-gold nanoparticles to the copoly (DMA-NAS-MAPS) solution for varying amount of time (4-10 hours).

Submerge a Si/$SiO_2$ chip in the solution of copoly(DMA-NAS-MAPS) and gold nanoparticles for 30 min on a shaker and then rinse thoroughly with DI water. Dry thoroughly with Argon/$N_2$ gas.

Bake the chip at 80° C. for 15 min. The gold nanoparticles are distributed randomly on $SiO_2$ surface, forming the assay plate.

Store the assay plate in a dry environment (e.g., vacuum desiccator).

Spotting with Offset.

Calibration nanoparticles can also be immobilized on the assay plate surface by spotting. Provided herein is an exemplary protocol to immobilize the calibration nanoparticles within patterned calibration regions that are offset from the probe regions:

Prepare a solution of copoly(DMA-NAS-MAPS) by adding 100 mg of the copolymer to 5 mL of deionized (DI) water and add 5 mL of 40% saturated ammonium sulfate (($NH_4)_2SO_4$) solution to reach a final concentration of 0.92 M.

Submerge a Si/$SiO_2$ chip in the solution of copoly(DMA-NAS-MAPS) for 30 min on a shaker and then rinse thoroughly with DI water. Dry thoroughly with Argon/$N_2$ gas.

Bake the chip at 80° C. for 15 min.

Using a micro-arrayer or other patterning device, spot calibration nanoparticles (e.g., 70 nm gold nanoparticles) with non-functionalized DNA.

Incubate for an hour.

Rinse thoroughly with DI water and dry thoroughly with Argon/$N_2$ gas.

Spot probe proteins in regions offset from the calibration regions.

Figure 3A:
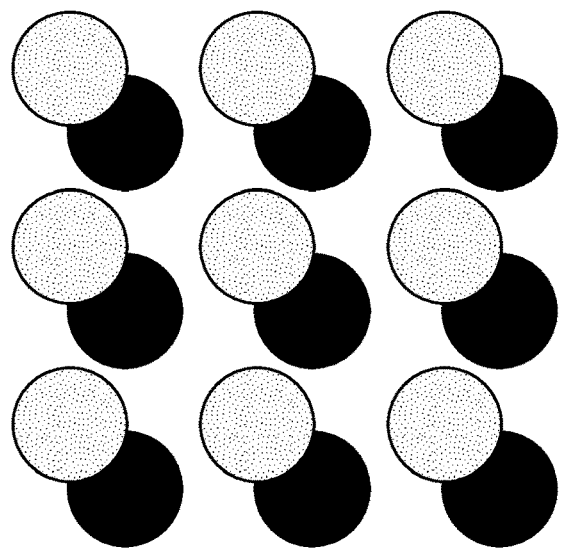
FIG. 3A is a schematic showing that the calibration regions are offset from the probe regions. The solid-filled circles indicate the probe regions, while the dot-filled circles indicate the calibration regions.
Figure 3B:
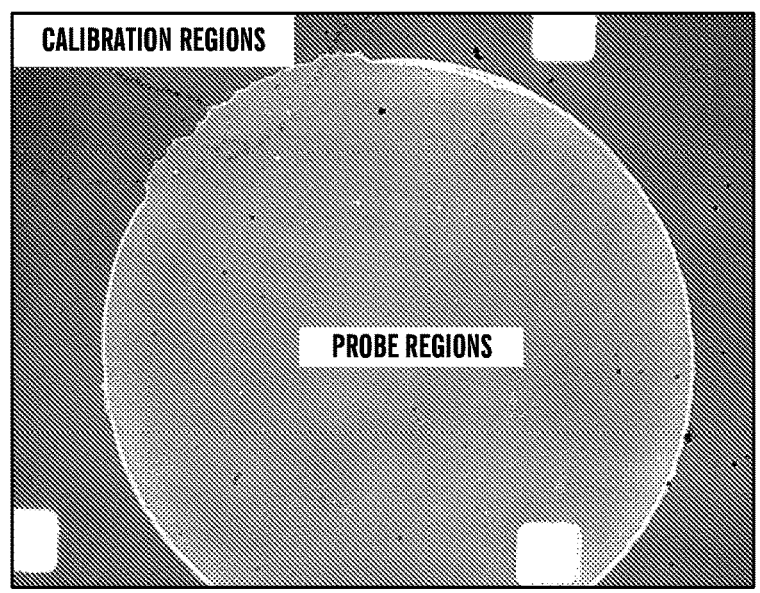
FIG. 3B is an image showing the results of the spotting.
Figure 4:
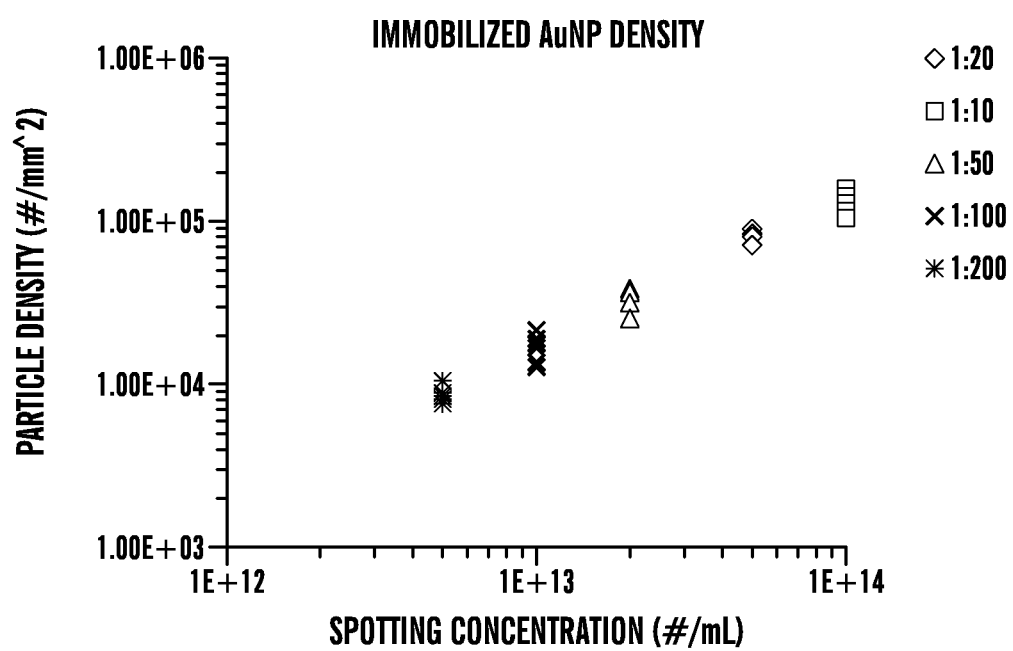
FIG. 4 shows that the density of gold nanoparticles can be tuned depending on the spotting concentration.

FIG. 3A is a schematic showing that the calibration regions are offset from the probe regions. FIG. 3B is an image showing the results of the spotting. FIG. 4 shows that the density of gold nanoparticles can be tuned depending on the spotting concentration.

Spotting without Offset.

Provided herein is an exemplary protocol to immobilize the calibration nanoparticles within patterned calibration regions that overlap with the probe regions:

Prepare a solution of copoly(DMA-NAS-MAPS) by adding 100 mg of the copolymer to 5 mL of deionized (DI) water and add 5 mL of 40% saturated ammonium sulfate (($NH_4)_2SO_4$) solution to reach a final concentration of 0.92 M.

Submerge a Si/$SiO_2$ chip in the solution of copoly(DMA-NAS-MAPS) for 30 min on a shaker and then rinse thoroughly with DI water. Dry thoroughly with Argon/$N_2$ gas.

Bake the chip at 80° C. for 15 min.

Using a micro-arrayer or other patterning device, spot calibration nanoparticles (e.g., 180 nm polystyrene nanoparticles) with non-functionalized DNA or anti-VSV antibodies.

Incubate for an hour.

Spot probe proteins in the same regions as the calibration regions.

Figure 5A:
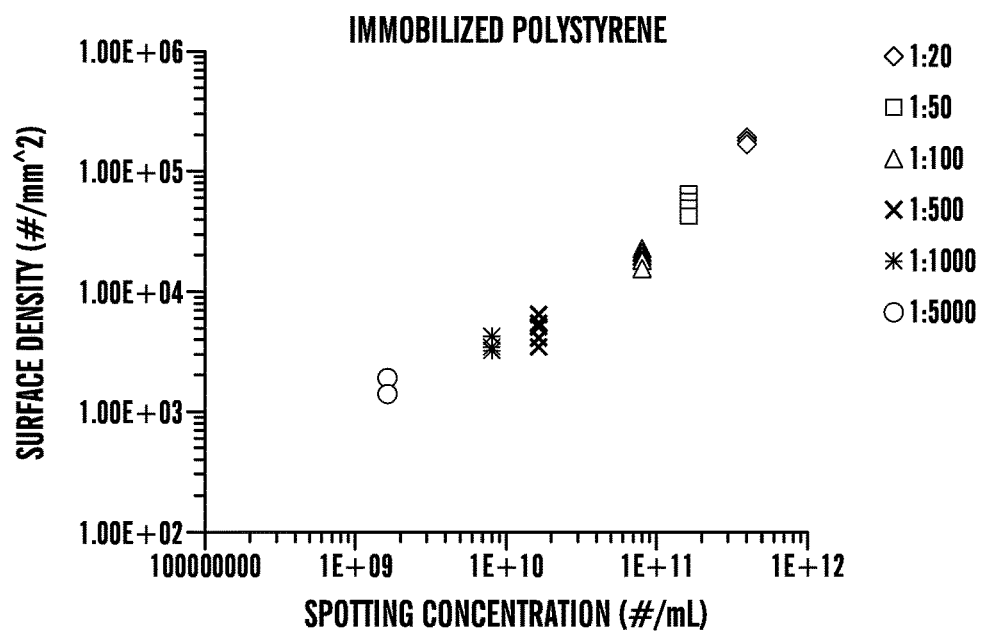
FIGS. 5A-5B show that the density of polystyrene nanoparticles can be tuned depending on the spotting concentration for (FIG. 5A) spotting with non-functionalized DNA, and (FIG. 5B) spotting with anti-VSV antibodies.
Figure 5B:
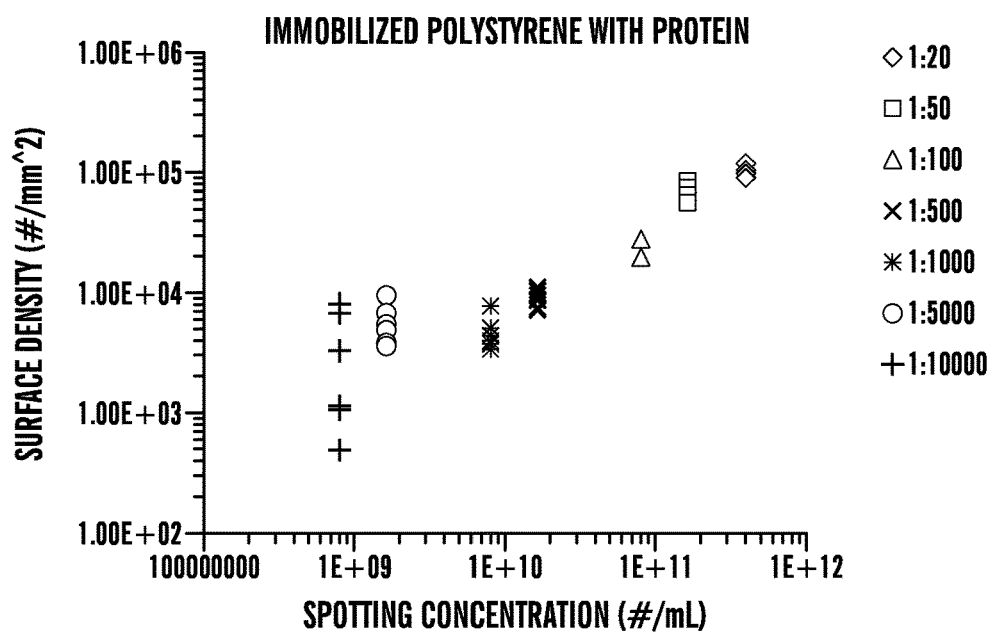
Figure 6:
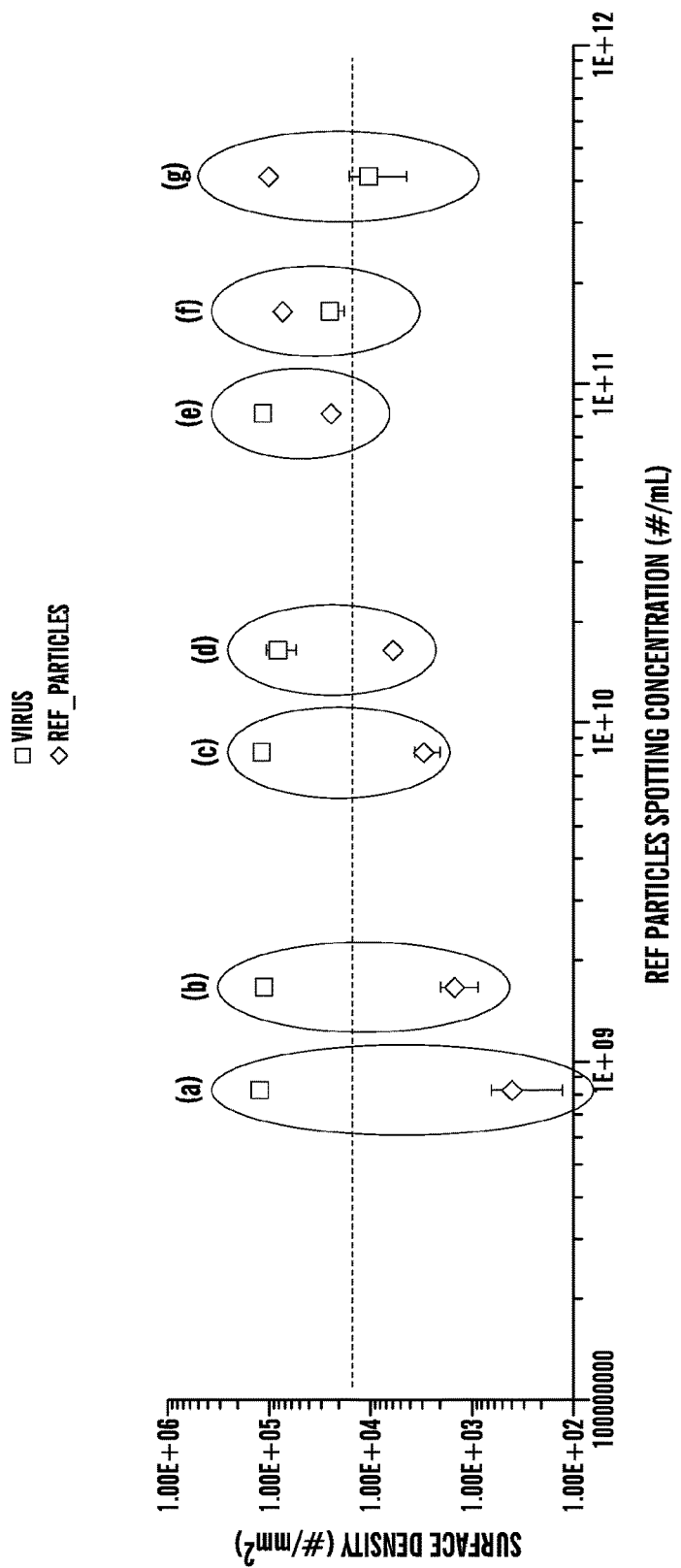
FIG. 6 shows that virus particles are captured in the regions containing calibration nanoparticles.
Figure 6:
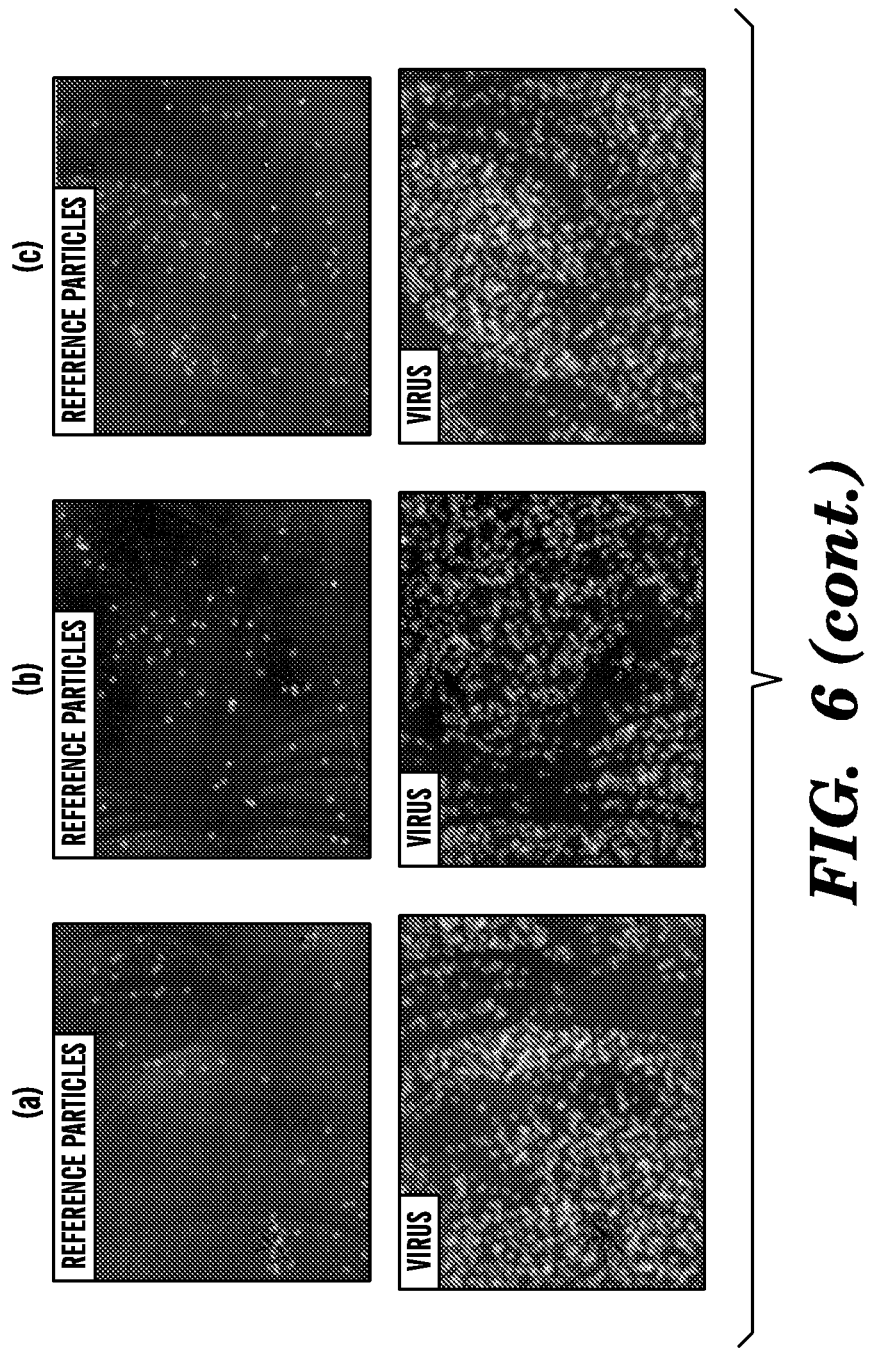
Figure 6:
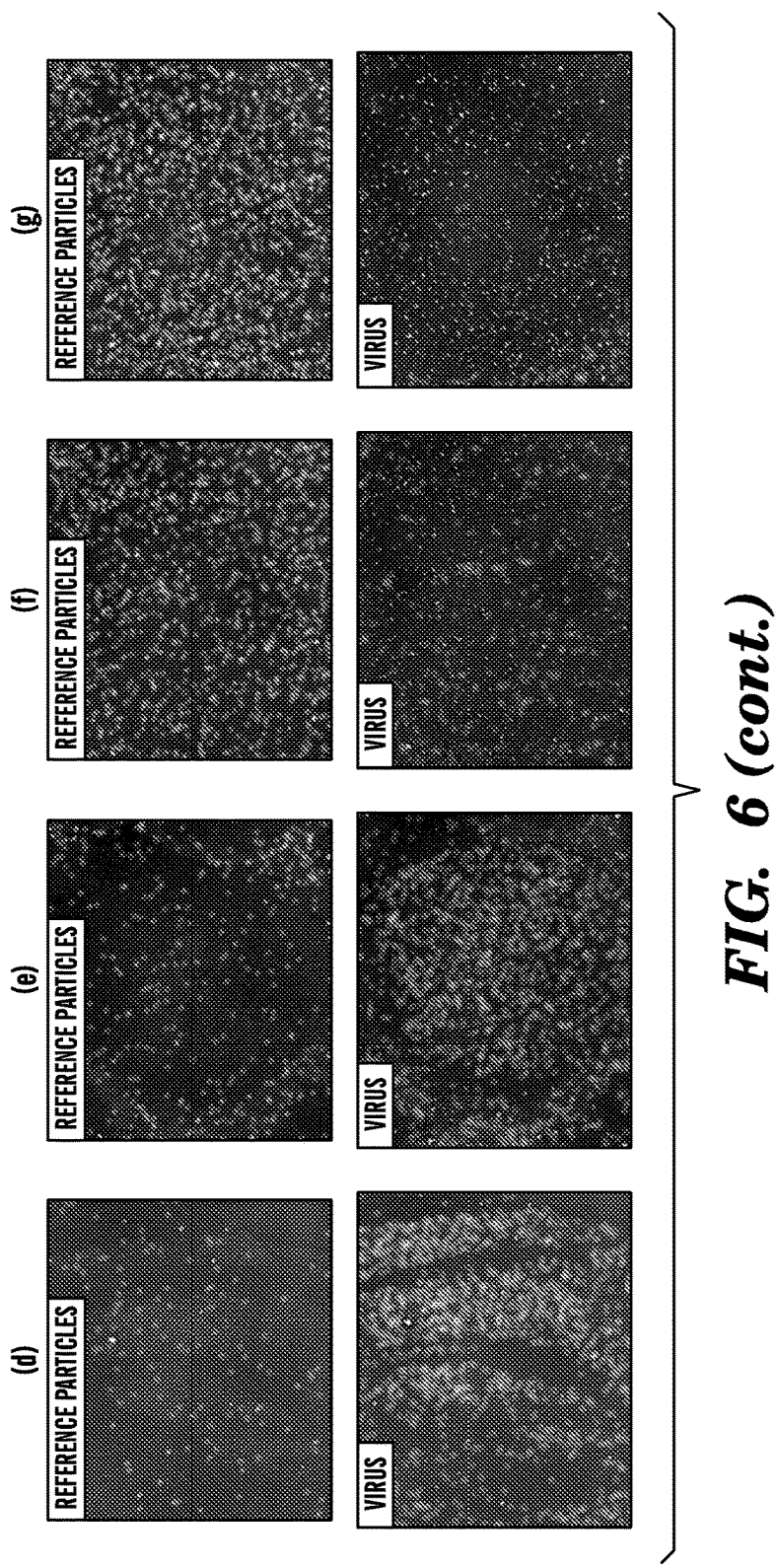

FIG. 5 shows that the density of polystyrene nanoparticles can be tuned depending on the spotting concentration for (A) spotting with non-functionalized DNA, and (B) spotting with anti-VSV antibodies. FIG. 6 shows that virus particles are captured in the regions containing calibration nanoparticles.

What is claimed is:
1. An assay plate comprising
(i) a base layer having a first reflective surface;
(ii) a transparent layer having a first surface in contact with the first reflective surface of the base layer, and a second surface providing a second reflective surface on the opposite side of the first surface, whereby the first and second reflective surfaces create an optical path length difference for light illuminating the assay plate; and (iii) at least one calibration nanoparticle having a pre-defined size immobilized in close proximity to the second surface of the transparent layer, whereby upon illumination, the sizes of the calibration nanoparticles can be determined as a function of the reflected light signal, and whereby the calibration nanoparticles are used as markers for autofocusing.

2. The assay plate of claim 1, wherein the first reflective surface is partially reflective, wherein the transparent layer is partially transparent and is less than 1000 nm thick, and wherein the calibration nanoparticles are placed in one or more calibration regions each having at least one calibration nanoparticle.

3. The assay plate of claim 1, wherein the reflectivity characteristics for the two reflective surfaces and the transparency characteristics for the transparent layer are selected to provide a measurable interferometric signal.

4. The assay plate of claim 1, wherein the base layer comprises silicon.

5. The assay plate of claim 1, wherein the transparent layer comprises silicon oxide.

6. The assay plate of claim 1, wherein the calibration nanoparticles are immobilized on the second surface of the transparent layer through an adhesive.

7. The assay plate of claim 6, wherein the adhesive includes a polymer.

8. The assay plate of claim 1, wherein the calibration nanoparticles are fabricated through lithography or focused ion beam.

9. The assay plate of claim 1, wherein the calibration nanoparticles have an average diameter in the range of 5 nm to 250 nm.

10. The assay plate of claim 1, further comprising periodic markers.

11. The assay plate of claim 1, further comprising probes on the same assay plate surface as the calibration nanoparticles, wherein the probes are antibodies, antigens, DNAs, RNAs, other macromolecules, and any combinations thereof.

12. A method of producing an assay plate, the assay plate including at least one calibration nanoparticle having a pre-defined size immobilized on a layered plate, wherein the layered plate comprises:
(i) a base layer having a first reflective surface;
(ii) a transparent layer having a first surface in contact with the first reflective surface of the base layer, and a second surface providing a second reflective surface on the opposite side of the first surface, whereby the first and second reflective surfaces create an optical path length difference for light illuminating the assay plate; and
the process comprising:
(i) immersing the layered plate in a polymer solution including calibration nanoparticles having a pre-defined size; and
(ii) washing the layered plate.

13. A method of producing assay plate, the assay plate including at least one calibration nanoparticle having a pre-defined size immobilized on a layered plate, wherein the layered plate comprises:
(i) a base layer having a first reflective surface;
(ii) a transparent layer having a first surface in contact with the first reflective surface of the base layer, and a second surface providing a second reflective surface on the opposite side of the first surface, whereby the first and second reflective surfaces create an optical path length difference for light illuminating the assay plate; and
the process comprising:
(i) immersing the layered plate in a polymer solution;
(ii) washing the layered plate; and
(iii) spotting with a patterning device calibration nanoparticles having a pre-defined size onto the polymer-coated layered plate.

14. A system comprising an assay plate according to claim 1 and an imaging system comprising:
(a) a microscope comprising an objective lens, an imaging device, and an illumination system, wherein the illumination system can separately produce at least three light sources each having a pre-defined center wavelength; and
(b) an autofocus system adapted for automatically adjusting the distance between the assay plate surface and the objective as a function of an image of at least one calibration nanoparticle.

15. The system of claim 14, wherein the illumination system comprises one or more light-emitting diodes (LEDs).

16. The system of claim 14, wherein the illumination system comprises a white light source and at least three spectral filters.

17. The system of claim 16, wherein the spectral filters can each produce a beam of light having a narrow wavelength range.

18. The system of claim 17, wherein the narrow wavelength range is 30 nm or less.

19. The system of claim 14, wherein the imaging device can capture a wide-field image.

20. The system of claim 14, wherein the imaging device includes a CCD camera.

21. The system of claim 20, wherein the CCD camera is monochromatic.

22. The system of claim 20, wherein the CCD camera is a color camera.

23. The system of claim 14, wherein the autofocus system includes a motorized module that moves the objective lens with respect to the assay plate.

24. The system of claim 14, wherein the autofocus system includes a motorized module that moves the assay plate with respect to the objective lens.

25. The system of claim 24, wherein the motorized module comprises a piezo motor.

26. The system of claim 24, wherein the motorized module comprises a stepper motor.

27. A method comprising
(i) providing an assay plate comprising at least one calibration nanoparticle having a pre-defined size, whereby the calibration nanoparticles are used for autofocusing;
(ii) illuminating with an illumination system the surface of the assay plate using one or more light sources, wherein each light source is centered around one pre-defined center wavelength;
(iii) imaging with an imaging device the light signal reflected from the assay plate surface and collected through an objective lens positioned at two or more different Z heights from the surface of the assay plate;
(iv) determining the size of each of the calibration nanoparticles;

(v) comparing the sizes of the calibration nanoparticles with a reference range, wherein the reference range is +10% to −10% of the average size of the calibration nanoparticles;
(vi) determining an optimal Z height, wherein the number of calibration nanoparticles falling within the reference range is maximized; and
(vii) adjusting with a motorized module the assay plate surface to the optimal Z height.

* * * * *